United States Patent
Jin et al.

(10) Patent No.: US 12,328,551 B2
(45) Date of Patent: *Jun. 10, 2025

(54) METHOD AND APPARATUS FOR AUTOMATIC CORRECTION OF REAL EAR MEASUREMENTS

(71) Applicant: Starkey Laboratories, Inc., Eden Prairie, MN (US)

(72) Inventors: Wenyu Jin, Eden Prairie, MN (US); Tim Schoof, Minneapolis, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/744,354

(22) Filed: Jun. 14, 2024

(65) Prior Publication Data
US 2024/0334136 A1    Oct. 3, 2024

Related U.S. Application Data

(63) Continuation of application No. 17/811,467, filed on Jul. 8, 2022, now Pat. No. 12,041,418.
(Continued)

(51) Int. Cl.
| | |
|---|---|
| *H04R 25/00* | (2006.01) |
| *H04R 1/10* | (2006.01) |
| *H04R 3/04* | (2006.01) |

(52) U.S. Cl.
CPC ......... *H04R 25/505* (2013.01); *H04R 1/1016* (2013.01); *H04R 1/1041* (2013.01);
(Continued)

(58) Field of Classification Search
CPC .. H04R 25/505; H04R 1/1016; H04R 1/1041; H04R 3/04; H04R 25/353; H04R 25/558; H04R 25/70; H04R 2430/03
(Continued)

(56) References Cited

U.S. PATENT DOCUMENTS

| | | |
|---|---|---|
| 2019/0082278 A1 | 3/2019 | Boley et al. |
| 2023/0009826 A1 | 1/2023 | Jin et al. |

(Continued)

FOREIGN PATENT DOCUMENTS

| | | |
|---|---|---|
| EP | 2234414 A2 | 9/2010 |
| EP | 2323553 B1 | 10/2012 |

(Continued)

OTHER PUBLICATIONS

"U.S. Appl. No. 17/811,467, Notice of Allowance mailed Mar. 18, 2024", 9 pgs.

(Continued)

*Primary Examiner* — Sean H Nguyen
(74) *Attorney, Agent, or Firm* — Schwegman Lundberg & Woessner, P.A.

(57) ABSTRACT

Disclosed herein are systems and methods for automatic correction of real ear measurements (REMs). A sound signal is produced through a receiver of a hearing device, and a sound pressure signal is sensed using a microphone placed inside the ear canal. The sound pressure signal is transformed to obtain a frequency response signal, a local minimum of the frequency response signal is detected above a programmable frequency level, and a spectral flatness of the frequency response signal is calculated in a selected frequency band surrounding the local minimum. If the spectral flatness is greater than a selected threshold value, acoustic correction is applied to the frequency response in the selected frequency band using an estimated transfer function to obtain a corrected sound pressure frequency response. The corrected sound pressure frequency response is used to modify, or make a recommendation to modify, a physical or operational characteristic of the hearing device.

20 Claims, 8 Drawing Sheets

Related U.S. Application Data (60) Provisional application No. 63/220,106, filed on Jul. 9, 2021.

(52) U.S. Cl.
CPC ............. *H04R 3/04* (2013.01); *H04R 25/353* (2013.01); *H04R 25/558* (2013.01); *H04R 25/70* (2013.01); *H04R 2430/03* (2013.01)

(58) Field of Classification Search
USPC .......................................................... 381/313
See application file for complete search history.

(56) References Cited

U.S. PATENT DOCUMENTS

| | | |
|---|---|---|
| 2023/0320903 A1 | 10/2023 | Kurihara |
| 2023/0328464 A1 | 10/2023 | Xu et al. |

FOREIGN PATENT DOCUMENTS

| | | |
|---|---|---|
| WO | WO-2007123052 A1 | 11/2007 |
| WO | WO-2010016925 A1 | 2/2010 |
| WO | WO-2013070192 A1 | 5/2013 |

OTHER PUBLICATIONS

"European Application Serial No. 22183805.5, Communication pursuant to Article 94(3) EPC mailed Feb. 29, 2024", 4 pgs.

"European Application Serial No. 22183805.5, Extended European Search Report mailed Dec. 9, 2022", 5 pgs.

Sankowsky-Rothe, Tobias, et al., "Prediction of Sound Pressure at the Ear Drum in Occluded Human Ears", Acta Acustica united with Acustica, 97(4), (2011), 656-668.

Schmidt, Sebastian, et al., "Measurement of equal-loudness contours using eardrum pressure as reference signal", Proceedings of Acoustics, (2008), 6 pgs.

Sinclair, Sheila, et al., "The Audioscan® RM500 Real-Ear Hearing Aid Analyzer: Measuring for a Successful Fit", Trends in Amplification, vol. 5, No. 2, (2001), 10 pgs.

U.S. Appl. No. 17/811,467, filed Jul. 8, 2022, Method and Apparatus for Automatic Correction of Real Ear Measurements.

METHOD AND APPARATUS FOR AUTOMATIC CORRECTION OF REAL EAR MEASUREMENTS

CROSS-REFERENCE TO RELATED APPLICATION

This patent application is a continuation of U.S. patent application Ser. No. 17/811,467, filed Jul. 8, 2022, which claims the benefit of U.S. Provisional Patent Application No. 63/220,106, filed Jul. 9, 2021, each of which are incorporated by reference herein in their entirety.

TECHNICAL FIELD

This document relates generally to hearing device systems and more particularly to methods and apparatus for automatic correction of real ear measurements (REMs) for hearing device applications.

BACKGROUND

Examples of hearing devices, also referred to herein as hearing assistance devices or hearing instruments, include both prescriptive devices and non-prescriptive devices. Specific examples of hearing devices include, but are not limited to, hearing aids, headphones, assisted listening devices, and earbuds.

Hearing aids are used to assist patients suffering hearing loss by transmitting amplified sounds to ear canals. In one example, a hearing aid is worn in and/or around a patient's ear. Hearing aids may include processors and electronics that improve the listening experience for a specific wearer or in a specific acoustic environment.

Hearing aid fitting and parameter adjustment may be dependent upon acoustic pressure at a wearer's eardrum while wearing the hearing aid, which is usually based upon REMs. However, REMs can be inaccurate due to a number of factors, such as microphone placement. Improved methods of correction of REMs are needed.

SUMMARY

Disclosed herein are systems and methods for automatic correction of real ear measurements (REMs) for hearing device applications. A sound signal is produced through a receiver of a hearing device placed inside an ear canal of a user. A sound pressure signal is sensed, in response to the sound signal, using a microphone placed inside the ear canal. The sound pressure signal is transformed to obtain a frequency response signal, a local minimum of the frequency response signal is detected above a programmable frequency level, and a spectral flatness of the frequency response signal is calculated in a selected frequency band surrounding the local minimum. If the spectral flatness is greater than a selected threshold value, acoustic correction is applied to the frequency response in the selected frequency band using an estimated transfer function to obtain a corrected sound pressure frequency response. The corrected sound pressure frequency response is used to modify an operational characteristic of the hearing device, or to make a recommendation for a modification of a physical or operational characteristic of the hearing device.

Various aspects of the present subject matter include a system including a hearing device having a receiver. The system is configured to produce a sound signal through the receiver of the hearing device placed inside an ear canal of a user. The system further includes one or more processors programmed to sense a sound pressure signal, in response to the sound signal, using a microphone placed inside the ear canal. The one or more processors are also programmed to transform the sound pressure signal to obtain a frequency response signal, detect a local minimum of the frequency response signal above a programmable frequency level, and calculate a spectral flatness of the frequency response signal in a selected frequency band surrounding the local minimum. If the spectral flatness is greater than a selected threshold value, the one or more processors are further programmed to apply acoustic correction to the frequency response in the selected frequency band using an estimated transfer function to obtain a corrected sound pressure frequency response. In some embodiments, the corrected sound pressure frequency response is used by the one or more processors to modify an operational characteristic of the hearing device. In other embodiments, the corrected sound pressure frequency response is used by the one or more processors to make a recommendation for a modification of a physical or operational characteristic of the hearing device.

This Summary is an overview of some of the teachings of the present application and not intended to be an exclusive or exhaustive treatment of the present subject matter. Further details about the present subject matter are found in the detailed description and appended claims.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

The present detailed description will discuss hearing devices generally, including earbuds, headsets, headphones and hearing assistance devices using the example of hearing aids. Other hearing devices include, but are not limited to, those in this document. It is understood that their use in the description is intended to demonstrate the present subject matter, but not in a limited or exclusive or exhaustive sense.

The present subject matter may be used in all situations in which a hearing aid or other in-the-ear device is placed in a user's ear, and some of its parameters (e.g., amplification gains) are adjusted, taking into account the individual acoustic characteristics of the user's ear, such as characteristics of the residual ear canal with the hearing aid or audio device in place inside the ear.

Audiological best-practices call for measurement of real ear measurements (REMs) or real-ear aided response (REAR) in each ear to be fitted with a hearing aid. REAR is a function of frequency at position of the eardrum for a specified sound field, with the hearing aid (and its acoustic coupling) in place and turned on. However, sound pressure at the eardrum of a listener produced by hearing aids can vary substantially for different ears.

These measurements traditionally require the use of dedicated apparatus for real-ear measurement system by trained professionals or audiologists, who insert a probe tube equipped with a microphone inside the user's ear canal, in close proximity to the eardrum, with the hearing aid inserted into the ear. The audiologist can then adjust the amount of gain provided by the hearing aid to match target amplification levels (for example, using hearing aid fitting software) to the levels actually delivered to the patient. It has been shown that improved word and phoneme recognition and words for average speech in quiet were reported for the REM adjusted-fitting in compared with manufacturer-fitted devices.

While it is best practice for audiologists to use REMs when fitting hearing aids, it is not always done in the clinic. Some reasons for this may be time constraints in the clinic, contraindications such as wax or patient discomfort, as well as difficulty with accurate probe tube placement. The present subject matter may be used with a hearing device having an inward facing ear canal microphone, instead of a probe tube microphone, in various embodiments.

The probe tube microphone is typically placed within 6-8 mm from the eardrum, using a fixed insertion depth from the inter-tragal notch (28 mm for women, 30 mm for men). A more accurate measurement could be made by placing the probe tube directly on the eardrum, but this would likely be too painful for the patient. One major issue with probe tube measurements taken from a fixed distance from the eardrum is artifacts in the response that result from standing waves in the ear canal due to ear canal acoustics that create notches (as shown in FIGS. 2A-2E) in the frequency responses resulting from these standing waves at high frequency ranges, typically beyond the first resonance peak at approximately 3 kHz to 4 kHz. These notches prevent an accurate measurement of the actual stimulus level at the eardrum, and thus cause an inaccurate measure of hearing aid gain that the patient is receiving.

The present subject matter solves the above problems by applying a correction factor to the notches, thereby providing a more accurate REM and allowing for more variable probe tube placement or the use of an in-the-ear-canal microphone of the device itself. In various embodiments, the present system and method receives input of sound pressure response data from a probe tube microphone or device microphone in the ear canal and eliminates the measurement artifacts due to quarter-wavelength notches, automatically outputting corrected sound pressure data at the eardrum which can be further used as a reference for calculation of real-ear insertion gain (REIG).

In addition, the present subject matter checks for the necessity for notch correction, as not all notches need to be corrected. Thus, the risk of improper correction that leads to even more significant errors is mitigated. In various embodiments, the present subject matter provides an individualized solution for a wearer or user of a hearing device. A correction model is used that is individualized for each subject, by searching based on measured data for an optimal parameter set for acoustic model, including length of acoustic cylinder and radii ratio at two ends of acoustic cylinder/cone model, in various embodiments. Thus, the present subject matter provides for acoustic leakage and venting estimation of hearing aids or other hearing devices, such as ear buds, and provides for improved sound quality for low-frequency audio delivered via hearing aids or ear buds (including music delivered via earphones).

Figure 1A:
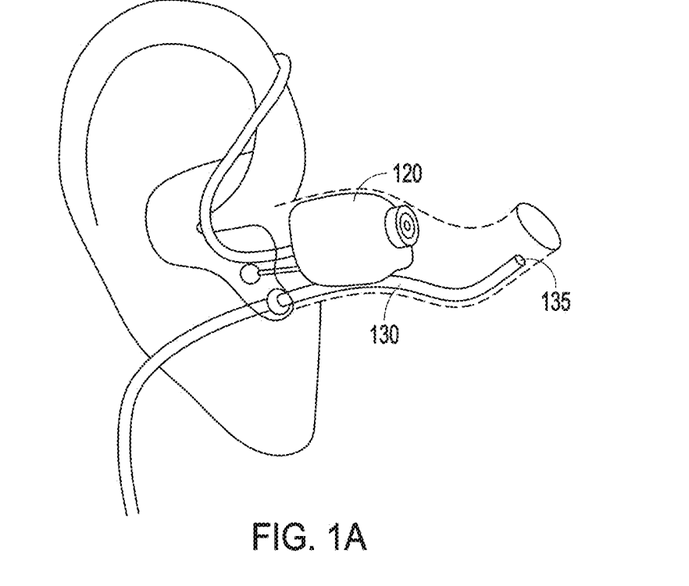
FIGS. 1A-1C illustrate systems for automatic correction of real ear measurements (REMs) for hearing device applications, according to various embodiments of the present subject matter.
Figure 1B:
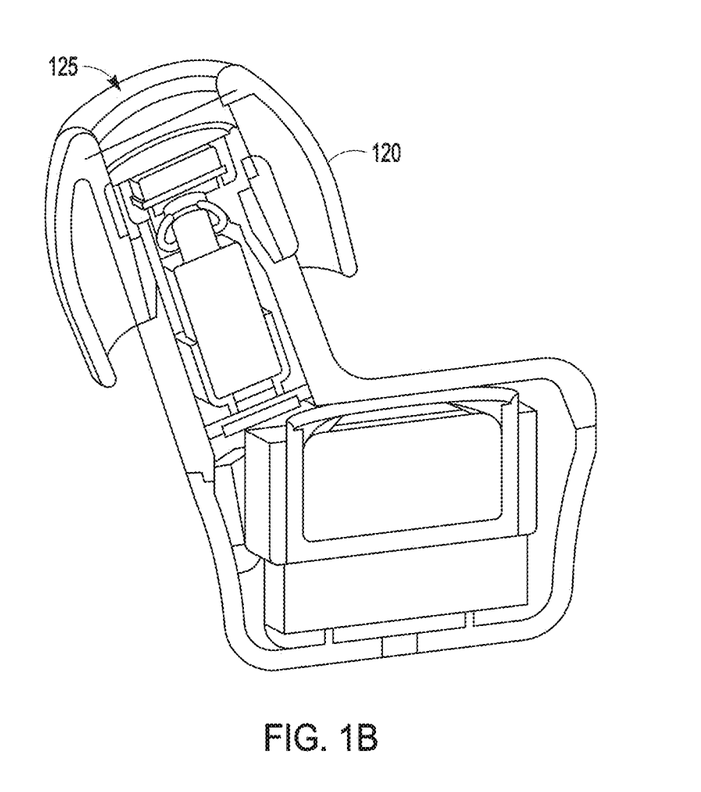

FIGS. 1A-1C illustrate systems for automatic correction of real ear measurements (REMs) for hearing device applications, according to various embodiments of the present subject matter. FIG. 1A illustrates an in-the-canal (ITC) type hearing device 120 being fitted in an ear canal of a wearer. In the depicted embodiment, a probe tube 130 having a microphone 135 at a distal end is positioned proximate the wearer's eardrum to detect a sound pressure signal during fitting of the hearing device 120. FIG. 1B illustrates a hearing device 120 having an inward facing microphone 125. The hearing device microphone 125 may be used, instead of or in addition to a probe tube microphone, to detect a sound pressure signal during fitting of the hearing device 120. Sound pressure at the eardrum of the wearer produced by hearing devices can vary substantially for different wearers. The automatic correction of REMs of the present subject matter can be used to provide a more accurate estimation of eardrum sound pressure and vent/leakage, facilitating a more accurate fitting and better fitting earbuds and vent size selection for each individual wearer.

Figure 1C:
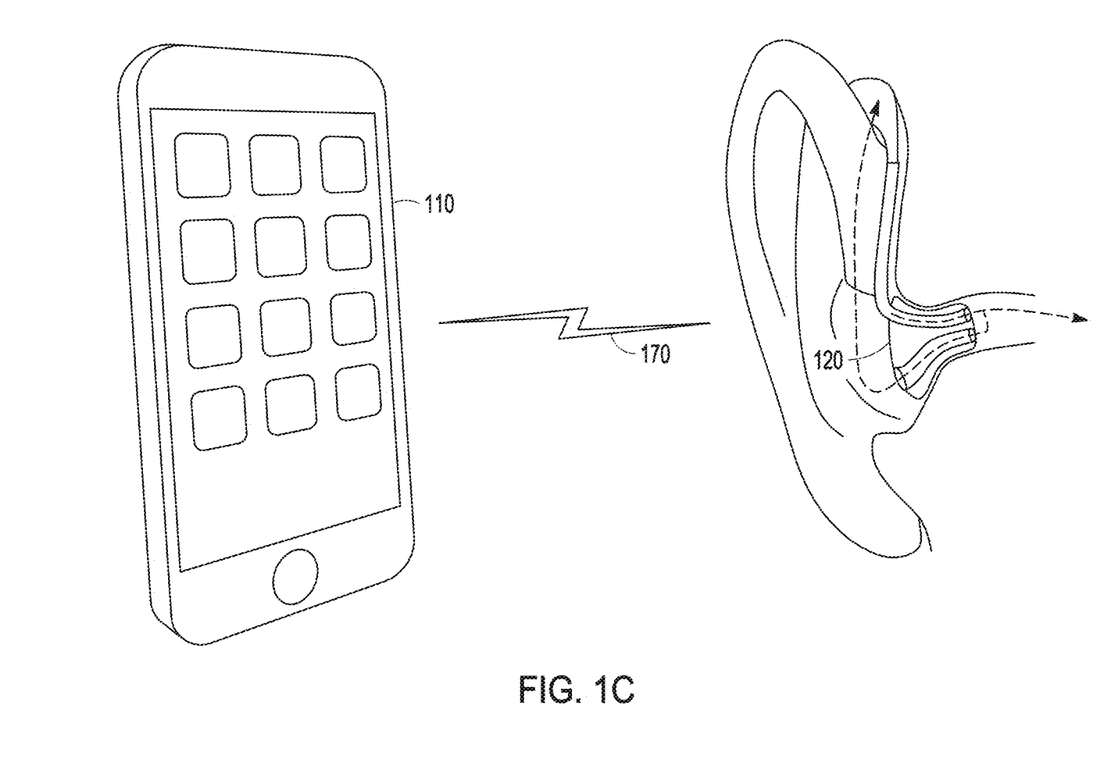

FIG. 1C illustrates a block diagram of a system for automatic correction of REMs for hearing devices, according to various embodiments of the present subject matter. The system may include an external device 110, such as a personal computer or smartphone, and a hearing device 120. Other types of external devices may be used without departing from the scope of the present subject matter. In various embodiments, the one or more processors for implementing the present algorithm may be in the hearing device 120, in the external device 110, or a combination of both the hearing device 120 and the external device 110. In some embodiments, an operational characteristic of the hearing device 120 is modified using the corrected real-ear response signal. In some embodiments, the corrected real-ear response signal is used to make a recommendation for a modification of a physical characteristic of the hearing device 120.

The hearing device 120 may communicate wirelessly 170 with the external device 110, or using a wired connection, to transmit data or audio for set up and programming the hearing device 120, in some embodiments. In some embodiments a wireless, non-acoustic audio stream may be transmitted from a wireless audio source to the hearing assistance device 120, which may be amplified and provided to a user as an acoustic output.

Figure 2A:
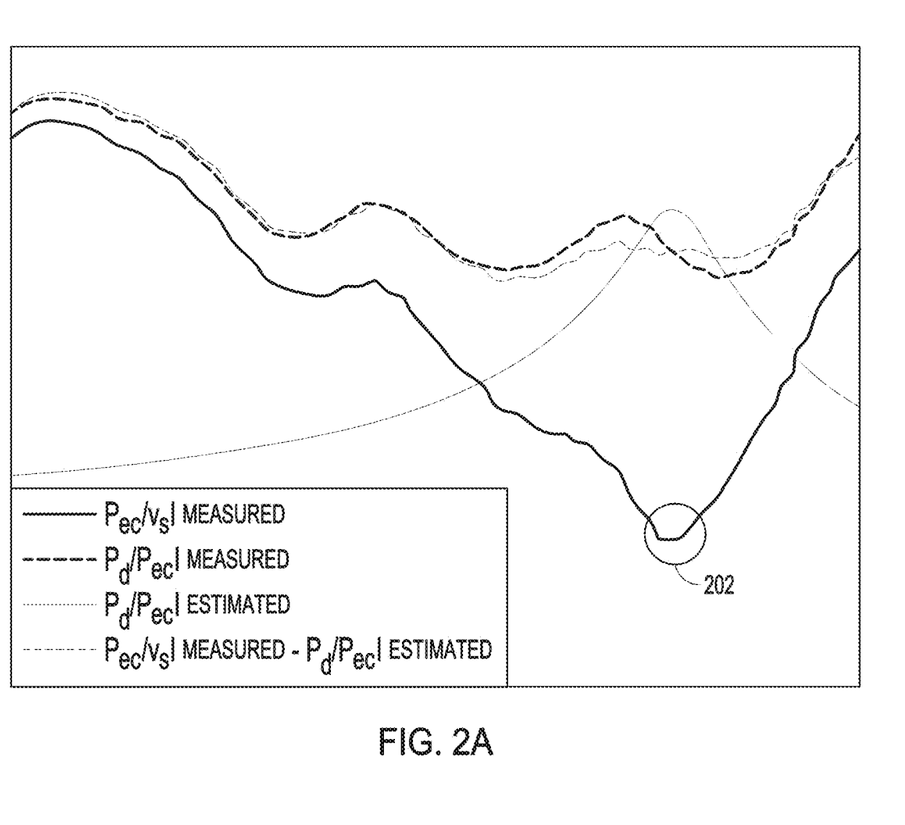
FIGS. 2A-2E illustrate graphical diagrams showing REMs and automatic correction of REMs for hearing devices, according to various embodiments of the present subject matter.

FIGS. 2A-2E illustrate graphical diagrams showing REMs and automatic correction of REMs for hearing devices, according to various embodiments of the present subject matter. As shown in FIG. 2A, probe-tube measures contain measurement artifacts due to quarter-wavelength notches 202 related to backward reflections. These minimas are related to the probe tube microphone measurement protocol in which a probe tube was inserted using a fixed insertion depth from the inter-tragal notch. In prior schemes, the fixed insertion depth was set to be 28 mm for women, 30 mm for men, and in an average adult, this insertion depth meant the probe tube tip was positioned within 6-8 mm from the eardrum. However, it is difficult to enforce the measurements with fixed distance to the eardrum among different subjects (e.g., inserted until touching at the eardrum, at which point the tube was then pulled back by the minimum amount).

The present system takes the input of the measured probe tube response data (or device microphone response data) and automatically outputs the corrected/approximated sound pressure data at the eardrum, thus correcting for variable distance from the microphone to the eardrum. In various embodiments, the present subject matter performs the steps of detecting the local minimum at high frequency ranges (i.e. >4 kHz), identifying the necessity for notch compensation by checking smoothness metric, and automatically correcting the acoustic notches due to standwave artifacts.

In various embodiments, to detect the local minimum of the response data s (k) at f_1m over frequencies beyond 4 kHz (k is wavenumber $$k = \frac{2\pi f}{c},$$

c is speed of sound).

In various embodiments, to conduct the smoothness calculation within the range of [f_1m−1000,f_1m+1000]. If $$\text{flatness} = \frac{\left(\prod_{k=b_1}^{b_2} s_k\right)^{\frac{1}{b_2-b_1}}}{\frac{1}{b_2-b_1}\sum_{k=b_1}^{b_2} s_k}$$

Where:

S (k) is the magnitude value of measured frequency response at bin k, and $b_1$=f_1m−1000 $b_2$=f_1m+1000 are the band edges, in bins.

In various embodiments, if the value of spectral flatness is larger than an emperical threshold (here chosen to be T1=0.4), then acoustic correction on this local minimum is need. Otherwise, no further correction is needed. Other thresholds may be used without departing from the scope of the present subject matter.

Figure 2B:
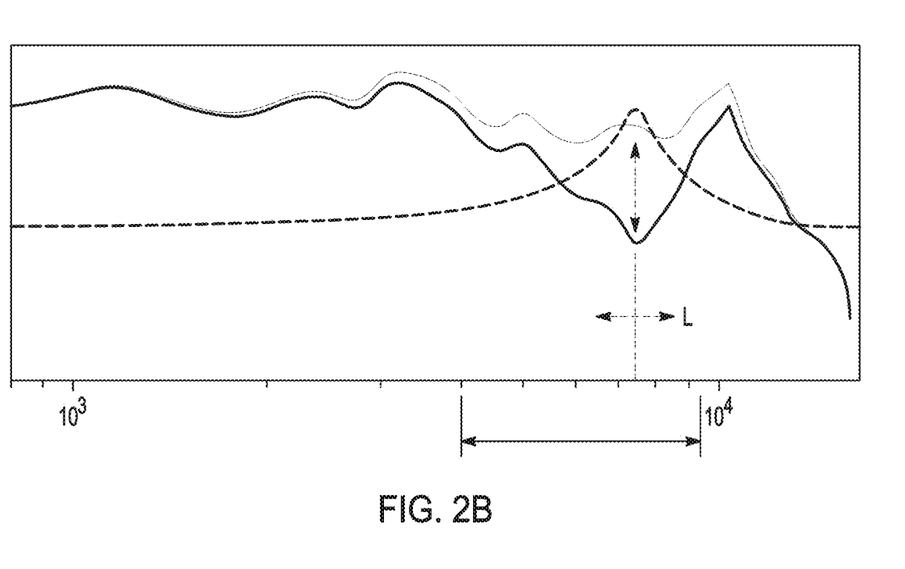

As shown in FIG. 2B, the corrected eardrum spectrum responses feature smooth functions of frequency such that the damping of the measured minimum is fully compensated. In various embodiments, a lossless truncated cone/cylinder model is used to model the pressure transfer function from the measurement position to the eardrum:

$$h(k, r_{ec}, L) = \frac{1}{\cos(kL) + j\left(\frac{r_d}{r_{ec}}\right)^2 \sin(kL)}$$

where r_ec is the ear canal radius at the position of probe tube measurement, L is the length of the cone/cylinder model ear canal, and r_d is the radius at the eardrum end and is set to 2.5 mm, in an embodiment.

According to various embodiments, the corrected eardrum sound pressure is derived as:

$$s'(k,r_{ec},L)=s(k)*h(k,r_{ec},L)$$

In various embodiments, an automatic iterative stepwise regression routine is used to automatically determine the key parameters of the model for smoothness optimization.

$\tau=\{k_j|j=b_1 \ldots b_2\}$ is a set of frequency bins for smoothness checking, $m(\tau,r_{ec},L)$ is the mean value of first derivative (i.e. gradient) of $s'(\tau,r_{ec},L)$ and $F(\tau,r_{ec},L)$ is the inverse of spectral flatness value of $s'(\tau,r_{ec},L)$.

In various embodiments, a target function is to find the parameter set that minimize the weighted sum of the mean value of first derivative (i.e., gradient) and the inverse of spectral flatness:

$$(\hat{r}_{ec}, \hat{L}) = \underset{(r_{ec},L)}{\arg\min} \lambda m(\tau, r_{ec}, L) + (1-\lambda)F(\tau, r_{ec}, L)$$

where $\Delta$ is a lagrange multiplier that balance the trade-off and weightings between $F(\tau,r_{ec},L)$ (which represents the spectral peakness) and $m(\tau,r_{ec},L)$ (which represents the horizontally unlevelness). In various embodiments of the present subject matter, a value of $\lambda=0.2$ is used.

In various embodiments, after the optimal parameter set $(\hat{r}_{ec},\hat{L})$ that minimizes the target function is found, and the final corrected sound pressure at the eardrum position is derived using:

$$s'(k)=s(k)*h(k,\hat{r}_{ec},\hat{L})$$

Figure 2C:
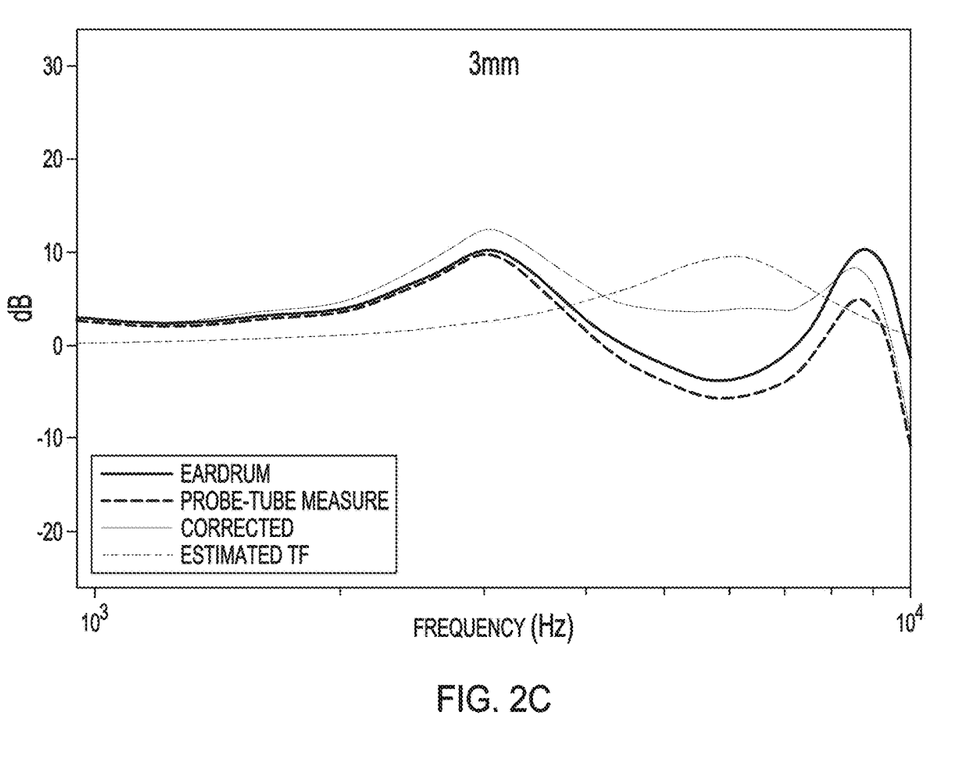
Figure 2D:
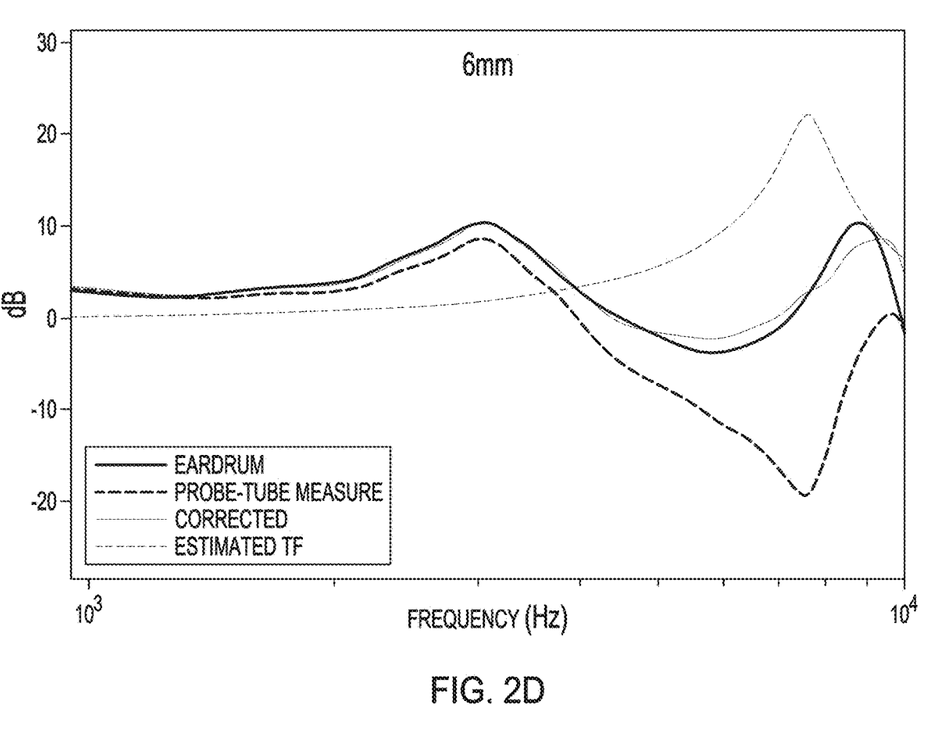
Figure 2E:
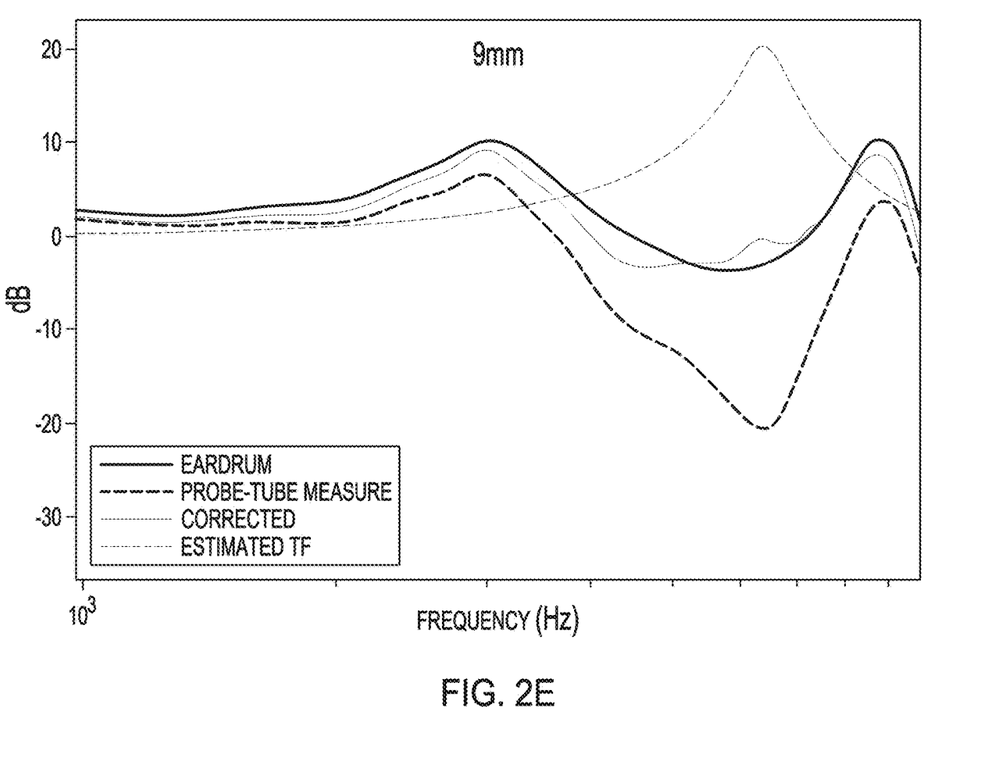

As shown in FIGS. 2C-2E, the estimate of the eardrum pressure is consistently well matched with the provided measured pressures at eardrum position for targeted frequency range (>4 kHz).

Figure 3:
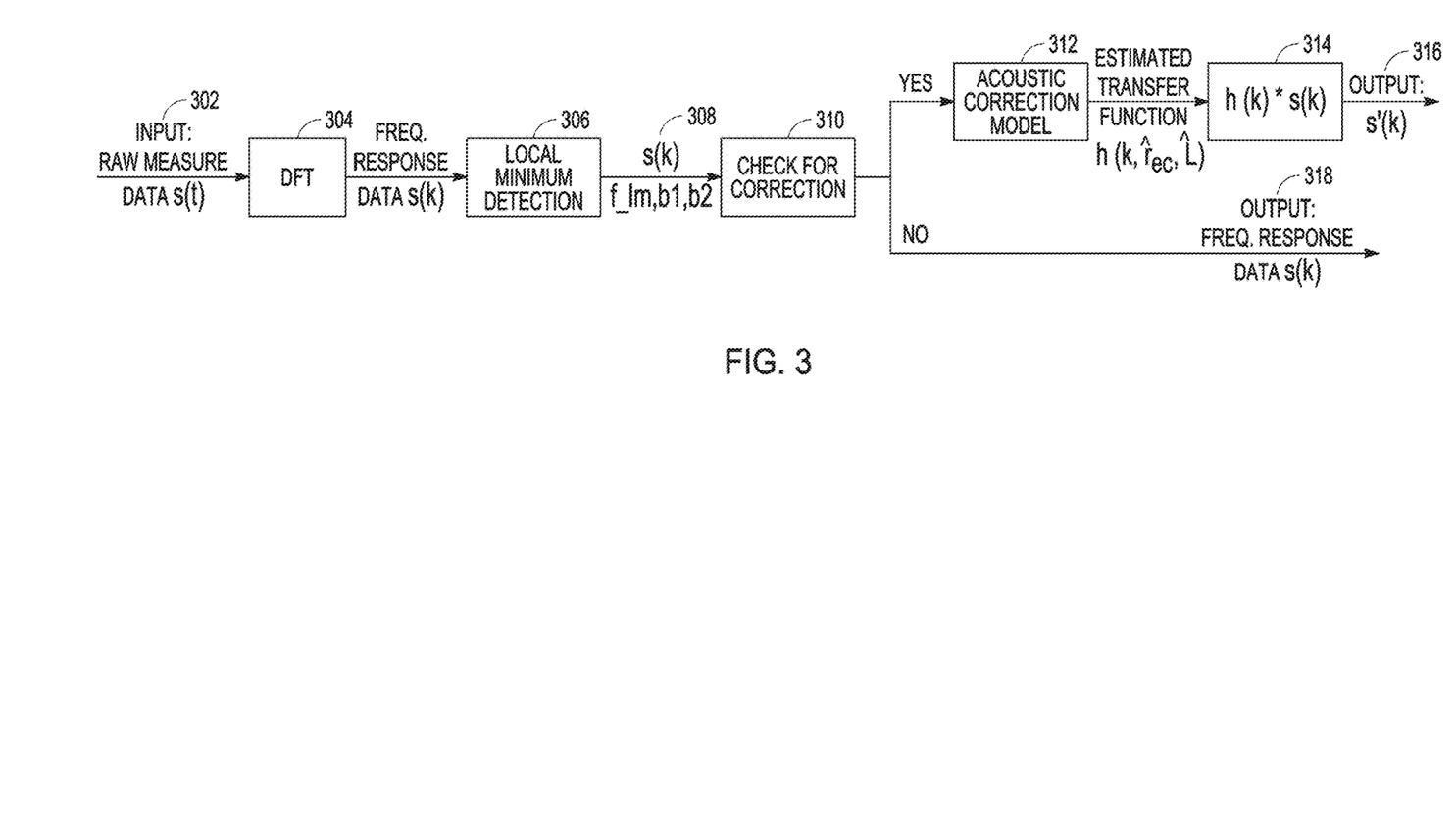
FIG. 3 illustrates a flow diagram of a method for automatic correction of REMs for hearing device applications, according to various embodiments of the present subject matter.

FIG. 3 illustrates a flow diagram of a method for automatic correction of REMs for hearing device applications, according to various embodiments of the present subject matter. A sound signal is produced through a receiver, or a physical extension of the receiver, placed inside an ear canal of a user. A sound pressure signal is sensed 302, in response to the sound signal, using a microphone placed inside the ear canal. The sound pressure signal is transformed 304 to obtain a frequency response signal, a local minimum of the frequency response signal is detected 306 above a programmable frequency level, and a spectral flatness of the frequency response signal is calculated 308 in a selected frequency band surrounding the local minimum. If the spectral flatness is greater than a selected threshold value 310, acoustic correction is applied 312 to the frequency response in the selected frequency band using an estimated transfer function 314 to obtain a corrected sound pressure frequency response 316. The corrected sound pressure frequency response 316 is used to modify an operational characteristic of the hearing device, or to make a recommendation for a modification of a physical or operational characteristic of the hearing device, in various embodiments. If the spectral flatness is not greater than a selected threshold value 310, the frequency response data is output 318 without correction.

According to various embodiments, applying acoustic correction to the frequency response includes removing measurement artifacts due to quarter-wavelength notches in the frequency response. The method includes using the corrected sound pressure frequency response as a reference for calculation of real-ear insertion gain (REIG), in various embodiments. In various embodiments, the estimated transfer function is based on a lossless truncated cone/cylinder model that is used to model the ear canal of the user. Applying acoustic correction includes using an automatic iterative stepwise regression routine, in some embodiments. In various embodiments, applying acoustic correction includes using a target function to determine a parameter set that minimizes a weighted sum of a mean value of a first derivative of the frequency response and an inverse of the spectral flatness. Applying acoustic correction to the frequency response includes multiplying the frequency response by the estimated transfer function to obtain the corrected sound pressure frequency response, in some embodiments. According to various embodiments, transforming the sound pressure signal includes using a discrete Fourier transform (DFT). The programmable frequency level is 4 kHz, in some embodiments. In various embodiments, the selected frequency band is from 1 kHz below to 1 kHz above the local minimum. The selected threshold value is 0.4, in various embodiments.

Various aspects of the present subject matter include a system including a hearing device including a receiver. The system is configured to produce a sound signal through the receiver of the hearing device, or a physical extension of the receiver, placed inside an ear canal of a user. The system further includes one or more processors programmed to sense a sound pressure signal, in response to the sound signal, using a microphone placed inside the ear canal. The one or more processors are also programmed to transform the sound pressure signal to obtain a frequency response signal, detect a local minimum of the frequency response signal above a programmable frequency level, and calculate a spectral flatness of the frequency response signal in a selected frequency band surrounding the local minimum. If the spectral flatness is greater than a selected threshold value, the one or more processors are further programmed to apply acoustic correction to the frequency response in the selected frequency band using an estimated transfer function to obtain a corrected sound pressure frequency response. In some embodiments, the corrected sound pressure frequency response is used by the one or more processors to modify an operational characteristic of the hearing device. In other embodiments, the corrected sound pressure frequency response is used by the one or more processors to make a recommendation for a modification of a physical or operational characteristic of the hearing device.

According to various embodiments, the one or more processors are included with the hearing device. The one or more processors are included in a personal computer or other external device in communication with the hearing device, in some embodiments. In various embodiments, the programmable frequency level is 4 kHz. The selected frequency band is from 1 kHz below to 1 kHz above the local minimum, in various embodiments. In some embodiments, the microphone is included with a probe tube measuring device. In some embodiments, the microphone is included with the hearing device. According to various embodiments, the hearing device includes one or more of a behind-the-ear (BTE), in-the-ear (ITE), in-the-canal (ITC), receiver-in-canal (RIC), invisible-in-canal (IIC) or completely-in-the-canal (CIC) type hearing aid.

The present subject matter provides for a number of benefits. For example, the present system may be used to provide more accurate real car measurements in hearing devices that have an inward facing microphone, or by using a probe tube without having to worry about insertion depth of a probe tube microphone. The present subject matter also provides correction factors for stimulus levels at the eardrum, especially at lower frequencies, that could result in better sound quality. In addition, the present subject matter can be used to provide accurate REMs at the eardrum with an inward facing microphone to facilitate accurate match-to-targets without the involvement of an audiologist.

In one example, the present subject matter may be used during hearing aid fitting, e.g., for automatic adjustment of hearing aid parameters such as amplification gains, in-situ audiometry stimulus levels, tinnitus masker band levels, etc., according to the hearing aid user's estimated real-car aided response (REAR).

In various embodiments, an algorithm is provided that can be implemented inside a hearing aid (in firmware or software) and/or in an external device, such as a personal computer or smartphone (in hearing aid fitting software).

Eardrum sound-pressure and/or vent-effect estimates obtained using the present subject matter can be used to automatically adjust parameters of the user's hearing aid, including but not limited to: amplification gains, low-frequency amplification applied to audio signals streamed into the hearing aid from another audio device, acoustic stimulus level for in-situ audiometry, or tinnitus-stimulus for acoustic therapy for tinnitus. Such automated adjustment of gains based on estimates of individual eardrum sound pressure can provide various benefits during the hearing device fitting process, including but not limited to: automated individualized adjustments of hearing device gains, and automated adjustment of stimulus levels during in-situ audiometry. In addition, the automated adjustments can be advantageous subsequent to the fitting process, by providing improved audio sound quality, improved loudness comfort, improved speech understanding, and improved tinnitus-masker efficacy/efficiency.

REARs refer to measurements of pressure inside the car canal, with the hearing aid positioned inside the car as it would during normal use, as opposed to real-ear unaided responses (REURs), which are measured with the user's ear canal unobstructed by a hearing aid.

As provided herein, a vent effect is the difference in sound pressure inside the ear canal, with the device in place, relative to some reference condition (e.g., completely occluded ear canal or completely open ear canal). The term 'vent' should not be interpreted to mean solely a vent in the traditional sense of an opening in a custom hearing aid, but rather any acoustic opening or leakage, such as might occur, for instance, in a receiver-in-canal (RIC) hearing-aid equipped with a stock earbud.

The present subject matter may be implemented in software, such as in the fitting software of a hearing aid or audio device running on a personal computer or any other electronic medium equipped with a processor (smartphone, tablet, or other device), or on a processor of the hearing aid or audio device itself.

According to various embodiments, making a recommendation for a modification of a characteristic of the hearing device includes making a recommendation for a modification of a physical characteristic of the hearing device. According to some embodiments, making a recommendation for a modification of a physical characteristic of the hearing device includes making a recommendation to change earbud size. Making a recommendation for a modification of a physical characteristic of the hearing device includes making a recommendation to increase vent size, in some embodiments. In some embodiments, making a recommendation for a modification of a physical characteristic of the hearing device includes making a recommendation to decrease vent size.

According to various embodiments, making a recommendation for a modification of a characteristic of the hearing device includes making a recommendation for a modification of an operational characteristic of the hearing device. In some embodiments, making a recommendation for a modification of an operational characteristic of the hearing device includes making a recommendation to increase gain of the hearing device. In other embodiments, making a recommendation for a modification of an operational characteristic of the hearing device includes making a recommendation to decrease gain of the hearing device.

Figure 4:
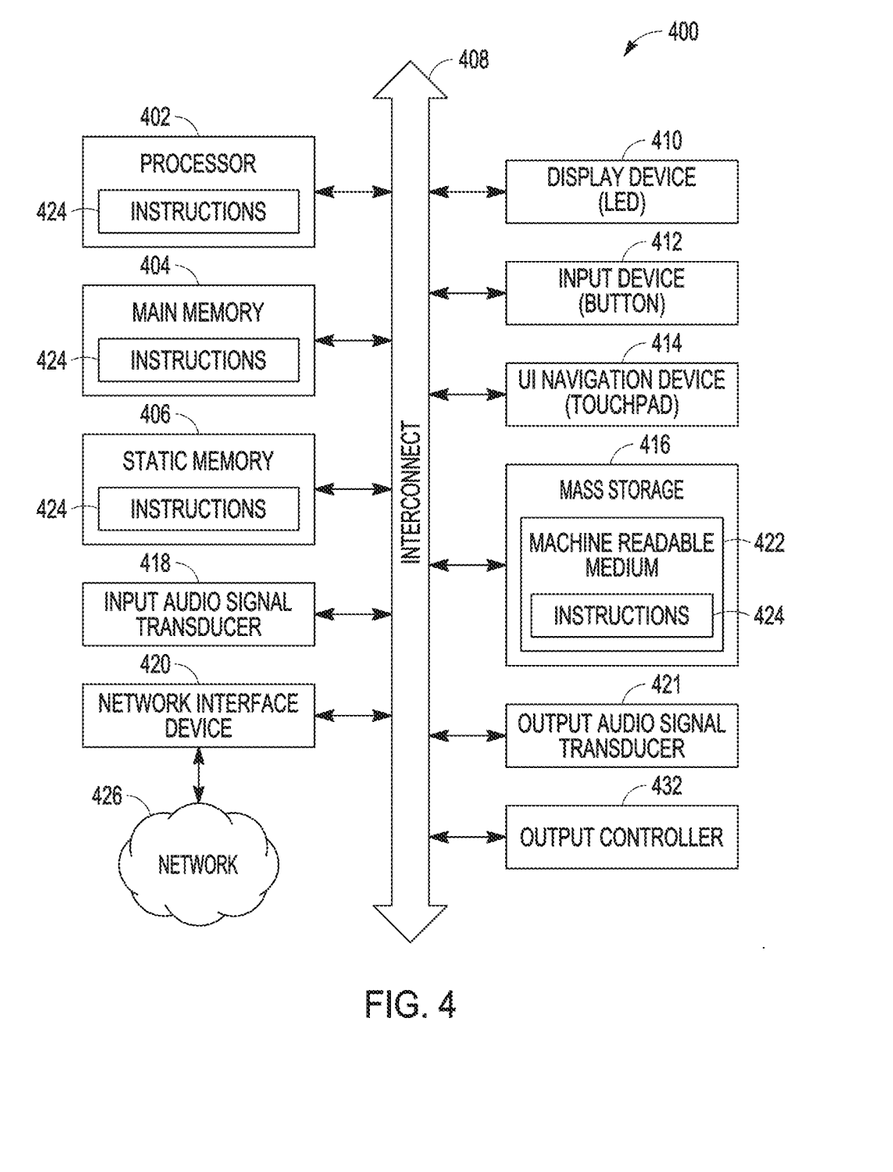
FIG. 4 illustrates a block diagram of an example machine upon which any one or more of the techniques discussed herein may perform.

FIG. 4 illustrates a block diagram of an example machine 400 upon which any one or more of the techniques (e.g., methodologies) discussed herein may perform. In alternative embodiments, the machine 400 may operate as a standalone device or may be connected (e.g., networked) to other machines. In a networked deployment, the machine 400 may operate in the capacity of a server machine, a client machine, or both in server-client network environments. In an example, the machine 400 may act as a peer machine in peer-to-peer (P2P) (or other distributed) network environment. The machine 400 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 400 may include a hardware processor 402 (e.g., a central processing unit (CPU), a graphics processing unit (GPU), a hardware processor core, or any combination thereof), a main memory 404 and a static memory 406, some or all of which may communicate with each other via an interlink (e.g., bus) 408. The machine 400 may further include a display unit 410, an alphanumeric input device 412 (e.g., a keyboard), and a user interface (UI) navigation device 414 (e.g., a mouse). In an example, the display unit 410, input device 412 and UI navigation device 414 may be a touch screen display. The machine 400 may additionally include a storage device (e.g., drive unit) 416, one or more input audio signal transducers 418 (e.g., microphone), a network interface device 420, and one or more output audio signal transducer 421 (e.g., speaker). The machine 400 may include an output controller 432, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 416 may include a machine readable medium 422 on which is stored one or more sets of data structures or instructions 424 (e.g., software) embodying or utilized by any one or more of the techniques or functions described herein. The instructions 424 may also reside, completely or at least partially, within the main memory 404, within static memory 406, or within the hardware processor 402 during execution thereof by the machine 400. In an example, one or any combination of the hardware processor 402, the main memory 404, the static memory 406, or the storage device 416 may constitute machine readable media.

While the machine readable medium 422 is illustrated as a single medium, the term "machine readable medium" may include a single medium or multiple media (e.g., a centralized or distributed database, and/or associated caches and servers) configured to store the one or more instructions 424.

The term "machine readable medium" may include any medium that is capable of storing, encoding, or carrying instructions for execution by the machine 400 and that cause the machine 400 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine-readable medium with a plurality of particles having invariant (e.g., rest) mass. Accordingly, massed machine-readable media are not transitory propagating signals. Specific examples of massed machine-readable media may include: nonvolatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 424 may further be transmitted or received over a communications network 426 using a transmission medium via the network interface device 420 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 420 may include one or more physical jacks (e.g., Ethernet, coaxial, or phone jacks) or one or more antennas to connect to the communications network 426. In an example, the network interface device 420 may include a plurality of antennas to communicate wirelessly using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 400, and includes digital or analog communications signals or other intangible medium to facilitate communication of such software.

Various embodiments of the present subject matter support wireless communications with a hearing device. In various embodiments the wireless communications may include standard or nonstandard communications. Some examples of standard wireless communications include link protocols including, but not limited to, Bluetooth™, Bluetooth™ Low Energy (BLE), IEEE 802.11 (wireless LANs), 802.15 (WPANs), 802.16 (WiMAX), cellular protocols including, but not limited to CDMA and GSM, ZigBee, and ultra-wideband (UWB) technologies. Such protocols support radio frequency communications and some support infrared communications while others support NFMI. Although the present system is demonstrated as a radio system, it is possible that other forms of wireless communications may be used such as ultrasonic, optical, infrared, and others. It is understood that the standards which may be used include past and present standards. It is also contemplated that future versions of these standards and new future standards may be employed without departing from the scope of the present subject matter.

The wireless communications support a connection from other devices. Such connections include, but are not limited to, one or more mono or stereo connections or digital connections having link protocols including, but not limited to 802.3 (Ethernet), 802.4, 802.5, USB, SPI, PCM, ATM, Fibre-channel, Firewire or 1394, InfiniBand, or a native streaming interface. In various embodiments, such connections include all past and present link protocols. It is also contemplated that future versions of these protocols and new future standards may be employed without departing from the scope of the present subject matter.

Hearing assistance devices typically include at least one enclosure or housing, a microphone, hearing assistance device electronics including processing electronics, and a speaker or "receiver." Hearing assistance devices may include a power source, such as a battery. In various embodiments, the battery is rechargeable. In various embodiments multiple energy sources are employed. It is understood that in various embodiments the microphone is optional. It is understood that in various embodiments the receiver is optional. It is understood that variations in communications protocols, antenna configurations, and combinations of components may be employed without departing from the scope of the present subject matter. Antenna configurations may vary and may be included within an enclosure for the electronics or be external to an enclosure for the electronics. Thus, the examples set forth herein are intended to be demonstrative and not a limiting or exhaustive depiction of variations.

It is understood that digital hearing assistance devices include a processor. In digital hearing assistance devices with a processor, programmable gains may be employed to adjust the hearing assistance device output to a wearer's particular hearing impairment. The processor may be a digital signal processor (DSP), microprocessor, microcontroller, other digital logic, or combinations thereof. The processing may be done by a single processor, or may be distributed over different devices. The processing of signals referenced in this application may be performed using the processor or over different devices. Processing may be done in the digital domain, the analog domain, or combinations thereof. Processing may be done using subband processing techniques. Processing may be done using frequency domain or time domain approaches. Some processing may involve both frequency and time domain aspects. For brevity, in some examples drawings may omit certain blocks that perform frequency synthesis, frequency analysis, analog-to-digital conversion, digital-to-analog conversion, amplification, buffering, and certain types of filtering and processing. In various embodiments of the present subject matter the processor is adapted to perform instructions stored in one or more memories, which may or may not be explicitly shown. Various types of memory may be used, including volatile and nonvolatile forms of memory. In various embodiments, the processor or other processing devices execute instructions to perform a number of signal processing tasks. Such embodiments may include analog components in communication with the processor to perform signal processing tasks, such as sound reception by a microphone, or playing of sound using a receiver (i.e., in applications where such transducers are used). In various embodiments of the present subject matter, different realizations of the block diagrams, circuits, and processes set forth herein may be created by one of skill in the art without departing from the scope of the present subject matter.

It is further understood that different hearing devices may embody the present subject matter without departing from the scope of the present disclosure. The devices depicted in the figures are intended to demonstrate the subject matter, but not necessarily in a limited, exhaustive, or exclusive sense. It is also understood that the present subject matter may be used with a device designed for use in the right ear or the left ear or both ears of the wearer.

The present subject matter is demonstrated for hearing devices, including hearing assistance devices, including but not limited to, behind-the-ear (BTE), in-the-ear (ITE), in-the-canal (ITC), receiver-in-canal (RIC), invisible-in-canal (IIC) or completely-in-the-canal (CIC) type hearing assistance devices. It is understood that behind-the-ear type hearing assistance devices may include devices that reside substantially behind the ear or over the ear. Such devices may include hearing assistance devices with receivers associated with the electronics portion of the behind-the-ear device, or hearing assistance devices of the type having receivers in the ear canal of the user, including but not limited to receiver-in-canal (RIC) or receiver-in-the-ear (RITE) designs. The present subject matter may also be used in hearing assistance devices generally, such as cochlear implant type hearing devices. The present subject matter may also be used in deep insertion devices having a transducer, such as a receiver or microphone. The present subject matter may be used in bone conduction hearing devices, in some embodiments. The present subject matter may be used in devices whether such devices are standard or custom fit and whether they provide an open or an occlusive design. It is understood that other hearing devices not expressly stated herein may be used in conjunction with the present subject matter.

This application is intended to cover adaptations or variations of the present subject matter. It is to be understood that the above description is intended to be illustrative, and not restrictive. The scope of the present subject matter should be determined with reference to the appended claims, along with the full scope of legal equivalents to which such claims are entitled.

What is claimed is:

1. A method, comprising:
sensing a sound pressure signal using a microphone placed inside an ear canal of a user of a hearing device;
transforming the sound pressure signal to obtain a frequency response;
detecting a local minimum of the frequency response above a programmable frequency level;
calculating a smoothness metric of the frequency response in a selected frequency band surrounding the local minimum;
automatically applying acoustic correction to the frequency response in the selected frequency band using an estimated transfer function to obtain a corrected sound pressure frequency response; and
using the corrected sound pressure frequency response to modify an operational characteristic of the hearing device, or to make a recommendation for a modification of a physical or operational characteristic of the hearing device.

2. The method of claim 1, wherein applying acoustic correction to the frequency response includes removing measurement artifacts due to quarter-wavelength notches in the frequency response.

3. The method of claim 1, comprising using the corrected sound pressure frequency response as a reference for calculation of real-ear insertion gain (REIG).

4. The method of claim 1, wherein the estimated transfer function is based on a lossless truncated cone/cylinder model that is used to model the ear canal of the user.

5. The method of claim 1, wherein applying acoustic correction includes using an automatic iterative stepwise regression routine.

6. The method of claim 1, wherein applying acoustic correction includes using a target function to determine a parameter set based on the frequency response and the smoothness metric.

7. The method of claim 1, wherein applying acoustic correction to the frequency response includes multiplying the frequency response by the estimated transfer function to obtain the corrected sound pressure frequency response.

8. The method of claim 1, wherein transforming the sound pressure signal includes using a discrete Fourier transform (DFT).

9. The method of claim 1, wherein the programmable frequency level is 4 kHz.

10. The method of claim 1, wherein the selected frequency band is from 1 kHz below to 1 kHz above the local minimum.

11. The method of claim 1, wherein the hearing device includes a hearing aid.

12. A system, comprising:
a hearing device; and
one or more processors programmed to:
sense a sound pressure signal using a microphone placed inside an ear canal;
transform the sound pressure signal to obtain a frequency response;
detect a local minimum of the frequency response above a programmable frequency level;
calculate a smoothness metric of the frequency response in a selected frequency band surrounding the local minimum;
automatically apply acoustic correction to the frequency response in the selected frequency band using an estimated transfer function to obtain a corrected sound pressure frequency response; and
use the corrected sound pressure frequency response to modify an operational characteristic of the hearing device, or to make a recommendation for a modification of a physical or operational characteristic of the hearing device.

13. The system of claim 12, wherein the one or more processors are included with the hearing device.

14. The system of claim 12, wherein the one or more processors are included in a personal computer in communication with the hearing device.

15. The system of claim 12, wherein the programmable frequency level is 4 kHz.

16. The system of claim 12, wherein the selected frequency band is from 1 kHz below to 1 kHz above the local minimum.

17. The system of claim 12, wherein the microphone is included with a probe tube measuring device.

18. The system of claim 12, wherein the microphone is included with the hearing device.

19. The system of claim 12, wherein the hearing device includes a hearing aid.

20. The system of claim 19, wherein the hearing aid includes one or more of a behind-the-ear (BTE), in-the-ear (ITE), in-the-canal (ITC), receiver-in-canal (RIC), invisible-in-canal (IIC) or completely-in-the-canal (CIC) type hearing aid.

* * * * *